United States Patent
Kitano

(10) Patent No.: US 8,602,979 B2
(45) Date of Patent: Dec. 10, 2013

(54) ELECTRONIC ENDOSCOPE HAVING FRONT-VIEW AND SIDE-VIEW IMAGE CAPTURING

(75) Inventor: Ryou Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 53 days.

(21) Appl. No.: 13/407,284

(22) Filed: Feb. 28, 2012

(65) Prior Publication Data

US 2012/0253121 A1    Oct. 4, 2012

(30) Foreign Application Priority Data

Mar. 31, 2011  (JP) .................................. 2011-079256

(51) Int. Cl.
| | | |
|---|---|---|
| A61B 1/05 | (2006.01) | |
| A61B 1/012 | (2006.01) | |
| A61B 1/06 | (2006.01) | |
| A61B 1/00 | (2006.01) | |

(52) U.S. Cl.
CPC ......... *A61B 1/00181* (2013.01); *A61B 1/00177* (2013.01); *A61B 1/00188* (2013.01); *A61B 1/0623* (2013.01)
USPC ........... 600/170; 600/129; 600/173; 600/167; 600/168

(58) Field of Classification Search
USPC .......... 600/167, 168, 170, 173, 129, 109, 107
See application file for complete search history.

(56) References Cited

U.S. PATENT DOCUMENTS

| | | | | |
|---|---|---|---|---|
| 4,741,327 A | * | 5/1988 | Yabe ............................. | 600/130 |
| 4,838,247 A | * | 6/1989 | Forkner ........................ | 600/173 |
| 4,846,154 A | * | 7/1989 | MacAnally et al. .......... | 600/171 |
| 4,868,644 A | * | 9/1989 | Yabe et al. ....................... | 348/76 |
| 5,782,751 A | * | 7/1998 | Matsuno ........................ | 600/157 |
| 5,940,126 A | * | 8/1999 | Kimura .......................... | 348/294 |
| 5,976,076 A | * | 11/1999 | Kolff et al. ..................... | 600/166 |
| 6,190,309 B1 | * | 2/2001 | Ooshima et al. .............. | 600/179 |
| 6,248,060 B1 | * | 6/2001 | Buess et al. ................... | 600/182 |
| 6,656,112 B2 | * | 12/2003 | Miyanaga ...................... | 600/179 |
| 2009/0062615 A1 | | 3/2009 | Yamaya | |
| 2009/0112061 A1 | * | 4/2009 | Kim et al. ...................... | 600/109 |

FOREIGN PATENT DOCUMENTS

| | | | |
|---|---|---|---|
| JP | 61-261713 | A | 11/1986 |
| JP | 3-269407 | A | 12/1991 |
| JP | 10-179516 | A | 7/1998 |
| JP | 10-311954 | A | 11/1998 |
| JP | 11-342104 | A | 12/1999 |
| JP | 2001-258822 | A | 9/2001 |
| JP | 2002-136472 | A | 5/2002 |
| JP | 2009-56105 | A | 3/2009 |
| JP | 2010-12079 | A | 1/2010 |

OTHER PUBLICATIONS

Machine translation of Matsuura et al., JP 10-179516, Jul. 1998.*

* cited by examiner

*Primary Examiner* — John P Leubecker
(74) *Attorney, Agent, or Firm* — Birch, Stewart, Kolasch & Birch, LLP.

(57) ABSTRACT

A distal portion of an electronic endoscope is formed with a cutaway portion and a distal end surface. The distal portion is provided with side-viewing and front-viewing capturing optical systems. The side-viewing capturing optical system has a side-viewing objective lens, a prism with a half mirror surface, and a varifocal lens. Light incident on the half-mirror surface from the side-viewing objective lens is reflected to be incident on a CCD through the varifocal lens. Moving the varifocal lens allows the side-viewing capturing optical system to switch from normal observation to magnifying observation and vice versa. In the magnifying observation, a best focus position resides on an extension, of an outer circumferential surface of the distal portion, facing the cutaway portion.

11 Claims, 6 Drawing Sheets

ELECTRONIC ENDOSCOPE HAVING FRONT-VIEW AND SIDE-VIEW IMAGE CAPTURING

BACKGROUND OF THE INVENTION

1. Field of the Invention

The present invention relates to an electronic endoscope for observing a target in a side-viewing direction perpendicular to an insertion direction of the electronic endoscope.

2. Description Related to the Prior Art

In the medical field, electronic endoscopes are used in various diagnoses and treatments. The electronic endoscope has an insert section to be inserted into a subject. A distal portion of the insert section is provided with a capturing optical system for taking in image light of a target in the subject and an image sensor for photoelectrically converting the image light taken in by the capturing optical system. Generally, an image capture window of the capturing optical system is disposed on a distal end surface of the distal portion to take in the image light in a front-viewing direction. The front-viewing direction is parallel with an insertion direction of the insert section.

There is a conventional electronic endoscope provided with a mechanism to vary a focal length of a capturing optical system so as to switch the focal length between normal and magnifying observation (for example, see Japanese Patent Laid-Open Publication No. 11-342104). When the normal observation is switched to the magnifying observation in a state that a distal end surface of a distal portion is positioned close to a target, a depth of field of the capturing optical system becomes shallow. As a result, it becomes difficult for the capturing optical system to focus on a target's surface.

To solve the problem, the electronic endoscope disclosed in the Japanese Patent Laid-Open Publication No. 11-342104 is provided with a hood attached to the distal portion of the insert section. The hood is used for ensuring a predetermined distance between the target's surface and the capturing optical system. The size of the hood is determined such that an end surface of the hood coincides with the best focus position of the capturing optical system. With the end surface of the hood coming in contact with the target's surface, the capturing optical system focuses on the target's surface.

When the electronic endoscope is inserted into a tract with a small diameter, for example, esophagus, it is difficult to change a direction of the distal portion. In this case, an electronic endoscope allowing observation in a radial direction (side-viewing direction) orthogonal to the insertion direction is used (see Japanese Patent Laid-Open Publications No. 2010-12079, No. 61-261713, No. 10-311954, and No. 3-269407). The electronic endoscopes disclosed in the Japanese Patent Laid-Open Publications No. 2010-12079 and No. 61-261713 allow observation in both the front-viewing and side-viewing directions. First, the endoscope is inserted into the subject and the observation in the front-viewing direction is performed. When an abnormal region is found, a side-viewing capturing optical system is brought close to the abnormal region to perform the observation in the side-viewing direction.

In the magnifying observation using the side-viewing capturing optical system of the endoscope disclosed in the Japanese Patent Laid-Open Publications No. 2010-12079, No. 61-261713, No. 10-311954, or No. 3-269407, it is difficult to focus on the target's surface when the distal end portion gets too close to the target's surface. To solve the problem, the Japanese Patent Laid-Open Publication No. 11-342104 discloses the hood for ensuring a predetermined distance between the capturing optical system and the target's surface as described above. However, the thickness of the hood increases the outer diameter of the distal portion. Additionally, to ensure a desired observation area of the side-viewing capturing optical system, the size of the hood needs to be increased in its radial direction. Thus, the hood increases the size of the distal portion.

SUMMARY OF THE INVENTION

An object of the present invention is to provide an electronic endoscope for facilitating focusing on a target's surface.

Another object of the present invention is to provide an electronic endoscope with a distal portion having a small diameter.

To achieve the above and other objects, an electronic endoscope of the present invention includes a cutaway portion, a side-viewing capturing optical system, a side lighting optical system, a focal length changer, and an image sensor. The cutaway portion is included in a distal portion of an insert section of the electronic endoscope and has a part of an outer circumferential surface of the distal portion cut away. The side-viewing capturing optical system forms an image of a target in a side-viewing direction through an image capture window provided to the cutaway portion. The side-viewing direction is orthogonal to an insertion direction of the insert section. The side lighting optical system applies illumination light to the target through a lighting window provided to the cutaway portion. The focal length changer changes a focal length of the side-viewing capturing optical system between a focal length for normal observation and a focal length for magnifying observation. The best focus position of the side-viewing capturing optical system in the magnifying observation resides on an extension of the outer circumferential surface. The extension faces the cutaway portion in the side-viewing direction. The image sensor captures the image formed by the side-viewing capturing optical system.

It is preferable that the cutaway portion is formed with a first surface orthogonal to the side-viewing direction and a second surface surrounded by the outer circumferential surface and the first surface. It is preferable that the second surface is inclined toward a front end side of the second surface. It is preferable that the image capture window is formed on the first surface, and the lighting window is formed on the second surface.

It is preferable that the side-viewing capturing optical system includes a side-viewing objective lens attached to the image capture window and an optical path changer for reflecting light from the side-viewing objective lens to the insertion direction so that the light is incident on the image sensor.

It is preferable that the electronic endoscope further includes a distal end surface of the distal portion, a front-viewing capturing optical system, and a half mirror surface being the optical path changer. The distal end surface is orthogonal to the insertion direction. The front-viewing capturing optical system forms an image of a target in a front-viewing direction. The front-viewing capturing optical system has a front-viewing objective lens provided on the distal end surface. The half mirror surface is disposed at an intersection of an optical axis of the side-viewing objective lens and an optical axis of the front-viewing objective lens. Light from the front-viewing objective lens passes through the half mirror surface to be incident on the image sensor.

It is preferable that the electronic endoscope further includes a front lighting optical system provided on the distal end surface, for illuminating the target observed with the front-viewing capturing optical system.

It is preferable that the electronic endoscope further includes a switcher for passing light from one of the front-viewing capturing optical system and the side-viewing capturing optical system and blocking light from the other of the front-viewing capturing optical system and the side-viewing capturing optical system.

It is preferable that the switcher is an LCD panel provided to each of the front-viewing capturing optical system and the side-viewing capturing optical system. The LCD panel is switchable between a blocking state and a passing state. The LCD panel blocks light in the blocking state and passes the light in the passing state.

It is preferable that the focal length changer is composed of a varifocal lens and a varifocal lens moving section for moving the varifocal lens along an optical axis of the varifocal lens. It is preferable that the varifocal lens is disposed between the optical path changer and the image sensor.

It is preferable that the extension of the outer circumferential surface resides within a depth of field of the side-viewing capturing optical system in the normal observation.

According to the present invention, in the magnifying observation with the side-viewing capturing optical system, the best focus position resides on the extension of the outer circumferential surface of the distal portion. This facilitates focusing on the target's surface and reduces the diameter of the distal portion.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
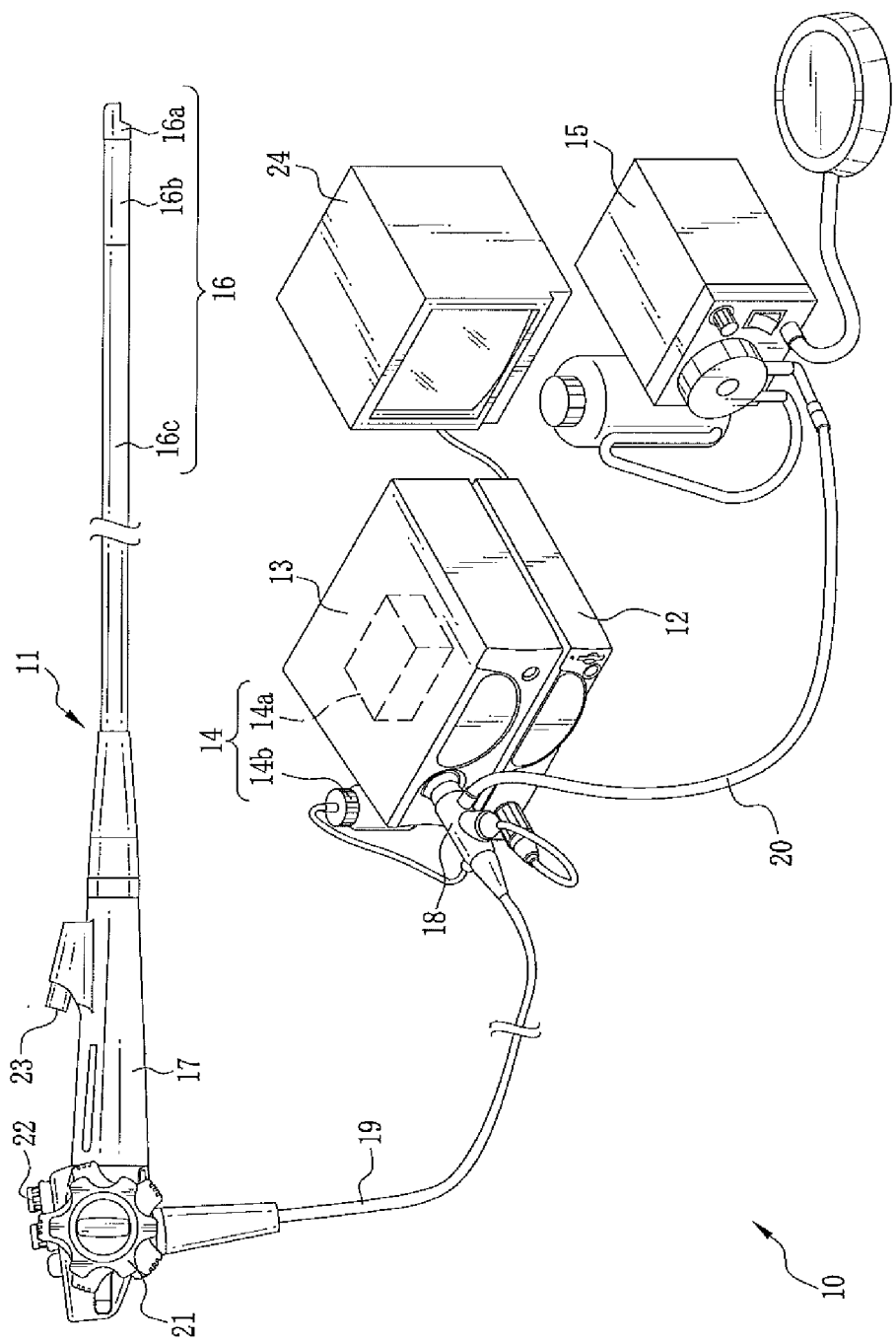
FIG. 1 is a perspective view of an electronic endoscope system.

In FIG. 1, an electronic endoscope system 10 is provided with an electronic endoscope 11, a processor device 12, a light source device 13, an air and water feeding device 14, and a liquid feeding device 15. The air and water feeding device 14 is provided to the light source device 13, and composed of a known air feeding device (for example, a pump) 14a and a water tank 14b provided externally to the light source device 13. The electronic endoscope 11 has an insert section 16, a handling section 17, a connector 18, and a universal cord 19. The insert section 16 is inserted into a subject. The handling section 17 is connected to a proximal end portion of the insert section 16. The connector 18 is of a complex type and connected to each of the processor device 12, the light source device 13, and the air and water feeding device 14. The connector 18 is also connected to the liquid feeding device 15 through a connection tube 20. The universal cord 19 connects the handling section 17 to the connector 18.

The insert section 16 is provided with a distal portion 16a, a flexible bending portion 16b, and a flexible tube portion 16c. The distal portion 16a is provided at a tip or distal end of the insert section 16. The distal portion 16a incorporates a CCD image sensor (hereinafter simply referred to as the CCD, see FIG. 3) 44. The bending portion 16b is connected to a proximal end of the distal portion 16a. The flexible tube portion 16c is connected to a proximal end of the bending portion 16b. The CCD 44 photoelectrically converts an image of a target formed on a light receiving surface into signal charge on a pixel-by-pixel basis. The signal charge accumulated in each pixel is read out and outputted as an imaging signal.

The handling section 17 is provided with operation members such as an angle knob 21 and air/water buttons 22. The angle knob 21 is used for bending the bending portion 16b in horizontal and vertical directions. The air/water buttons 22 are used for spraying air and/or water from an air/water nozzle 36 (see FIG. 2). The handling section 17 is provided with a forceps inlet 23 for inserting a medical instrument, for example, an electric scalpel in a forceps channel (not shown).

The processor device 12 is electrically connected to the light source device 13. The processor device 12 controls the operation of the whole electronic endoscope system 10. The processor device 12 supplies power to the electronic endoscope 11 through a transmission cable (not shown) extending through the universal cord 19, the insert section 16, and the like. The processor device 12 controls the operation of the CCD 44, LCD panels 45 and 46, and the like. The processor device 12 obtains the imaging signal outputted from the CCD 44 through the transmission cable. The processor device 12 performs various image processes to the imaging signal to generate image data. The image data is displayed as an observation image on a monitor 24 cable-connected to the processor device 12.

Figure 2:
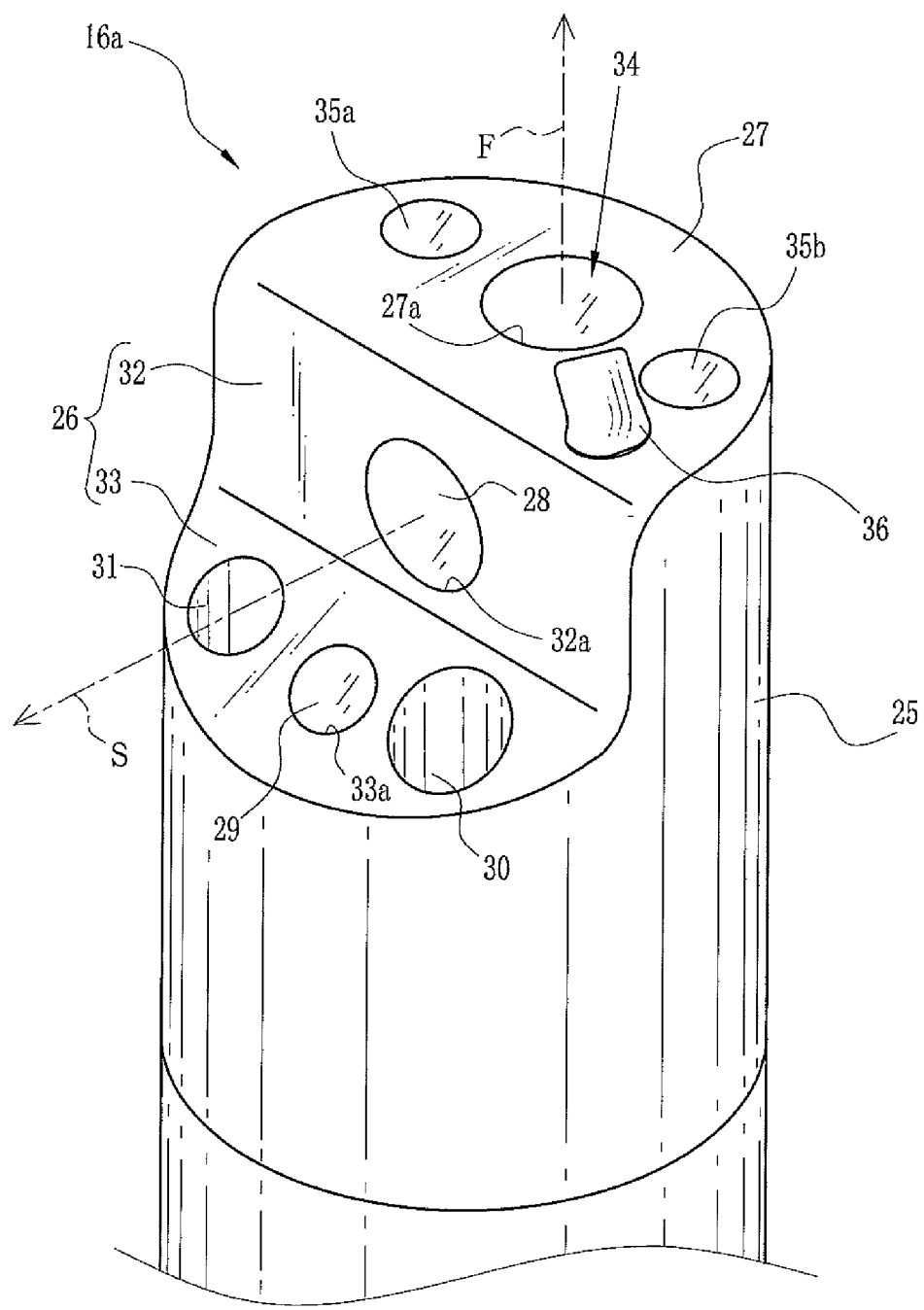
FIG. 2 is a perspective view of a distal portion of the electronic endoscope.

As shown in FIG. 2, the distal portion 16a is formed with a distal end surface 27 and a narrow portion or cutaway portion 26 having a part of an outer circumferential surface (cylindrical outer surface) 25 of the distal portion 16a (in other words, a part of the distal portion 16a including the outer circumferential surface 25) cut away or removed. The distal end surface 27 is a front end surface of the distal portion 16a.

On the cutaway portion 26, a side-viewing objective lens 28, a side lighting lens 29 being a side lighting optical system, a forceps outlet 30, and a water jet outlet 31 are provided. The side-viewing objective lens 28 constitutes a side-viewing capturing optical system 47 (see FIG. 3) which will be described later. An optical axis of the side-viewing objective lens 28 extends in a side-viewing direction S orthogonal to an insertion direction of the insert section 16.

The cutaway portion 26 includes a first surface (vertical plane) 32 and a second surface (inclined plane) 33. The first surface 32 is planar and orthogonal to the side-viewing direction S. The second surface 33 is surrounded by the outer circumferential surface 25 and the first surface 32. The second surface 33 is planar and inclined toward its front end. The side-viewing objective lens 28 is attached to an image capture window 32a formed on the first surface 32 such that an incident surface of the side-viewing objective lens 28 is flush with the first surface 32. The side-viewing objective lens 28 takes in image light in the side-viewing direction S.

The side lighting lens 29 is attached to a lighting window 33a formed on the second surface 33. Behind the side lighting lens 29, an exit end of a light guide 37a (see FIG. 3) faces the side lighting lens 29. The side lighting lens 29 applies illumination light, guided through the light guide 37a, to aside observation area that is a view field of the side-viewing capturing optical system 47.

On the second surface 33, the side lighting lens 29 is positioned between the forceps outlet 30 and the water jet outlet 31. The forceps outlet 30 is connected to the forceps inlet 23 of the handling section 17 through a forceps channel (not shown). The medical instrument is inserted into the forceps inlet 23 and projected from the forceps outlet 30, through the forceps channel, to be used for treatment.

The water jet outlet 31 is used for spraying a liquid, for example, wash water or a liquid medicine to a target (hereinafter referred to as the side target) in the side-viewing direction S. The water jet outlet 31 is connected to a water jet channel (not shown). The water jet channel extends through the insert section 16, the handling section 17 and the universal cord 19. The water jet channel is connected to the liquid feeding device 15 through the connection tube 20. The water jet outlet 31 is formed in a direction orthogonal to the second surface 33. Thereby, the water jet outlet 31 directly applies the liquid, send out from the liquid feeding device 15 to the water jet channel through the connection tube 20, to the side target.

The distal end surface 27 is planar and orthogonal to the insertion direction and connected to a front end of the first surface 32 of the cutaway portion 26. On the distal end surface 27, a front-viewing objective lens 34 constituting a front-viewing capturing optical system 48 (see FIG. 3) which will be described later, front lighting lenses 35a and 35b constituting a front lighting optical system, and the air/water nozzle 36 are provided. An optical axis of the front-viewing objective lens 34 extends in a front-viewing direction F parallel with the insertion direction. Note that the distal end surface 27 is orthogonal to the front-viewing direction F.

The front-viewing objective lens 34 is attached to an image capture window 27a on the distal end surface 27 such that an incident surface of the front-viewing objective lens 34 is flush with the distal end surface 27. The front-viewing objective lens 34 takes in image light from a target (hereinafter may be referred to as the front target) positioned in the front-viewing direction F.

The front lighting lenses 35a and 35b are positioned symmetrically with respect to the front-viewing objective lens 34. Behind the front lighting lens 35a, an exit end of a light guide 37b (see FIG. 4) faces the front lighting lens 35a. Behind the front lighting lens 35b, an exit end of alight guide 37c (see FIG. 4) faces the front lighting lens 35b. The front lighting lenses 35a and 35b apply the illumination light, guided by the respective light guides 37b and 37c, to a front observation area that is a view field of the front-viewing capturing optical system 48.

Each of the light guides 37a to 37c is an optical fiber bundle, composed of a plurality of optical fibers (made from quartz, for example), covered with a tube. The light guides 37a to 37c extend through the insert section 16, the handling section 17, the universal cord 19, and the connector 18. The light guide 37a guides the illumination light from the light source device 13 to the side lighting lens 29. The light guides 37b and 37c guide the illumination light from the light source device 13 to the respective front lighting lenses 35a and 35b.

The air/water nozzle 36 sprays air or wash water, supplied from the air and water feeding device 14, to the front-viewing objective lens 34 to wash off contamination on the front-viewing objective lens 34.

Figure 3:
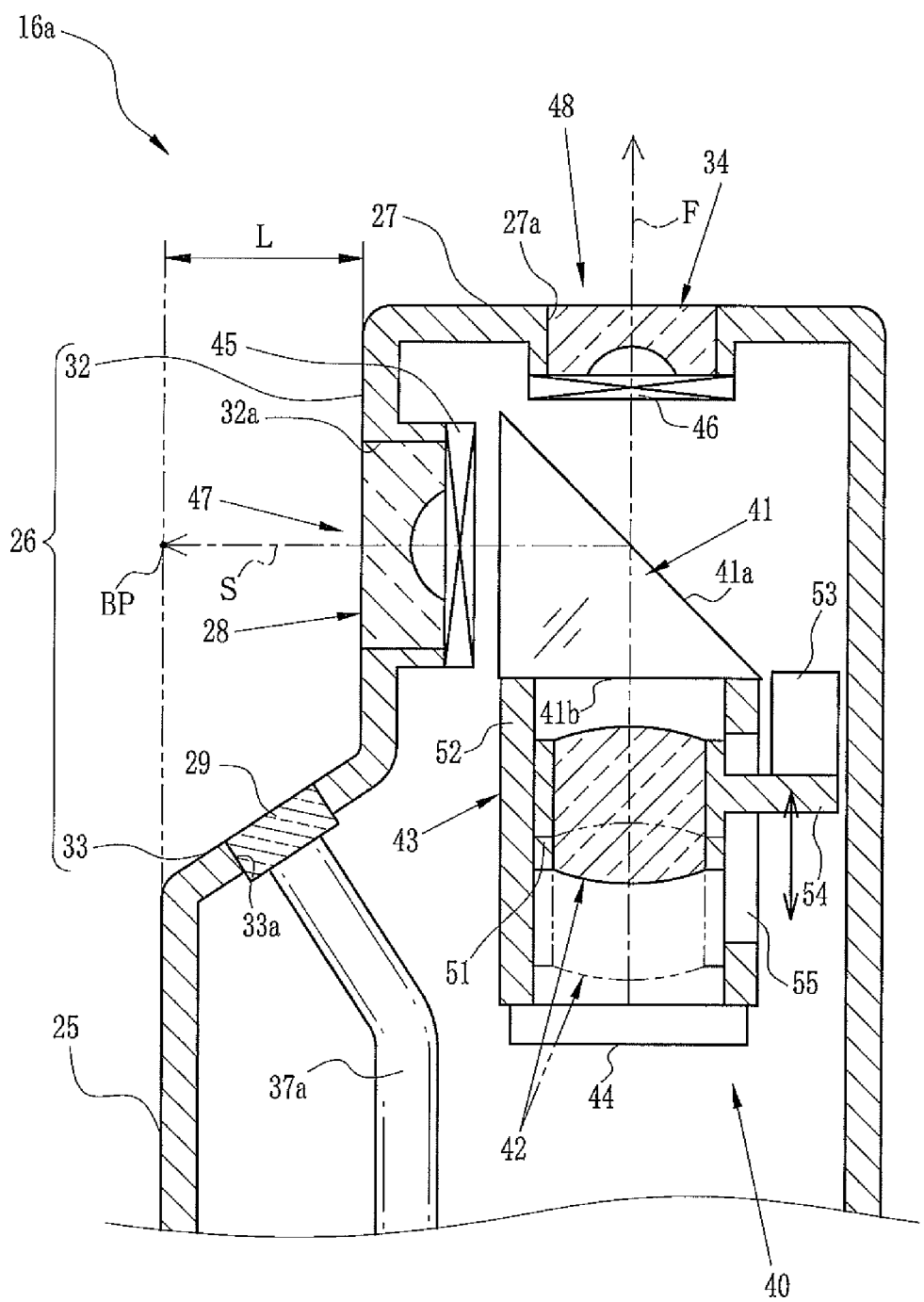
FIG. 3 is a cross-sectional view of a distal portion cut along side-viewing and front-viewing optical systems.

As shown in FIG. 3, the distal portion 16a incorporates an imaging section 40. The imaging section 40 is provided with the side-viewing objective lens 28, the front-viewing objective lens 34, a prism (optical path changer) 41, a varifocal lens 42, a lens moving mechanism 43, the CCD 44, and the LCD panels 45 and 46.

The imaging section 40 is composed of the side-viewing capturing optical system 47 and the front-viewing capturing optical system 48. Here, the side-viewing capturing optical system 47 and the front-viewing capturing optical system 48 share the varifocal lens 42. In other words, the side-viewing capturing optical system 47 is composed of the side-viewing objective lens 28, the prism 41, and the varifocal lens 42. The front-viewing capturing optical system 48 is composed of the front-viewing objective lens 34 and the varifocal lens 42, because the prism is not a requisite for the front-viewing capturing optical system 48.

The prism 41 is an isosceles right triangular prism. A half mirror surface 41a is formed on the prism's hypotenuse opposite to the right angle. The light incident on the prism reflects from or passes through the half mirror surface 41a. The half mirror surface 41a is positioned at an intersection of the optical axis of the side-viewing objective lens 28 and the optical axis of the front-viewing objective lens 34. The half mirror surface 41a is positioned at 45° apart from each of the optical axis of the side-viewing objective lens 28 and the optical axis of the front-viewing objective lens 34. Accordingly, the light incident on the half mirror surface 41a from the side-viewing objective lens 28 is reflected and then comes out of an exit surface 41b. The light incident on the half mirror surface 41a from the front-viewing objective lens 34 passes through the half mirror surface 41a and then comes out of the exit surface 41b.

The CCD 44 is positioned on an exit surface 41b side of the prism 41 and on the optical axis of the front-viewing objective lens 34. The CCD 44 is disposed parallel with the side-viewing direction S and orthogonal to the front-viewing direction F. The varifocal lens 42 is positioned between the exit surface 41b of the prism 41 and the CCD 44. The light passed through the prism 41 from the front-viewing objective lens 34 and the light reflected by the half mirror surface 41a from the side-viewing objective lens 28 is incident on a light receiving surface (not shown) of the CCD 44 through the varifocal lens 42. An image formed by each of the front-viewing and side-viewing capturing optical system 47 and 48 can be converted into an imaging signal.

The LCD panel 45 is disposed behind the side-viewing objective lens 28. The LCD panel 46 is disposed behind the front-viewing objective lens 34.

An LCD driver 63 (see FIG. 4) controls the LCD panels 45 and 46 and switches each of the LCD panels 45 and 46 between a passing state and a blocking state. When the LCD panel 45 is in the passing state, the LCD panel 45 allows the light from the side-viewing objective lens 28 to pass therethrough. When the LCD 46 is in the passing state, the LCD panel 46 allows the light from the front-viewing objective lens 34 to pass therethrough. When the LCD panel 45 is in the blocking state, the LCD panel 45 blocks the light from the side-viewing objective lens 28. When the LCD panel 46 is in the blocking state, the LCD panel 46 blocks the light from the front-viewing objective lens 34. The LCD panels 45 and 46 are put into the passing state when a predetermined voltage is applied. In the passing state, the whole surfaces of the LCD panels 45 and 46 exhibit the highest optical transmittance. The LCD panels 45 and 46 are put into the blocking state when the voltage is not applied. Alternatively, the LCD panels 45 and 46 may be put into the blocking state with the application of voltage. The LCD panels 45 and 46 may be put into the passing state when there is no voltage applied.

In observing the target, one of the LCD panels 45 and 46 is put into the passing state and the other is put into the blocking state to select one of the side-viewing capturing optical system 47 and the front-viewing capturing optical system 48 to be used. In other words, when the LCD panel 45 is put into the passing state, and the LCD panel 46 is put into the blocking state, the electronic endoscope 11 is in a side-viewing observation mode. On the other hand, when the LCD panel 45 is put into the blocking state, and the LCD panel 46 is put into the passing state, the electronic endoscope 11 is in a front-viewing observation mode.

The varifocal lens 42 and the lens moving mechanism 43 constitute a focal length changer. The lens moving mechanism 43 moves the varifocal lens 42 forward and backward along the optical axis direction to vary focal lengths of the side-viewing capturing optical system 47 and the front-viewing capturing optical system 48. The lens moving mechanism 43 is composed of a movable barrel 51 being a lens holder for holding the varifocal lens 42, a stationary barrel 52 being a guide member for guiding the movable barrel 51, and an actuator 53. The stationary barrel 52 is fixed inside the distal portion 16a such that an axis direction of the stationary barrel 52 is parallel with the optical axis of the varifocal lens 42. The CCD 44 is fixed at the rear end of the stationary barrel 52.

The movable barrel 51 fits into the stationary barrel 52 in a slidable manner to guide the varifocal lens 42 in the optical axis direction. The movable barrel 51 is integrally provided with a connection portion 54. The connection portion 54 protrudes from the stationary barrel 52 through a slit 55 in the stationary barrel 52. The actuator 53, for example, a solenoid is connected to the movable barrel 51 through the connection portion 54. The actuator 53 moves the movable barrel 51 and the varifocal lens 42 in the forward and backward directions.

In the lens moving mechanism 43, an actuator driver 64 (see FIG. 4) controls the actuator 53. Thereby, the actuator 53 moves the varifocal lens 42 to vary the focal length of the side-viewing capturing optical system 47 or the front-viewing capturing optical system 48 between a focal length for normal observation and a focal length for magnifying observation. In the magnifying observation, the focal length is longer than that in the normal observation. Hereinafter, a position of the varifocal lens 42 in the normal observation is referred to as the normal observation position (shown by two-dot chain lines in FIG. 3). A position of the varifocal lens 42 in the magnifying observation is referred to as the magnifying observation position (shown by solid lines in FIG. 3).

As described above, the surface of the side-viewing objective lens 28 is flush with the first surface 32 on the distal portion 16a. A distance L in the side-viewing direction S, that is, a distance between the surface of the side-viewing objective lens 28 and an extension (virtual extended line), of the outer circumferential surface 25, is equivalent to a depth (cut-away amount) of the cutaway portion 26 in the side-viewing direction S. The distance L is set such that the best focus position BP of the side-viewing capturing optical system 47 resides on the extension facing the cutaway portion 26 in the side-viewing direction S when the magnifying observation is performed with the side-viewing capturing optical system 47, namely, when the varifocal lens 42 is in the magnifying observation position.

On the other hand, when the varifocal lens 42 is in the normal observation position, the best focus position of the side-viewing capturing optical system 47 is not positioned on the extension of the outer circumferential surface 25. However, the distance L is set such that the extension, of the outer circumferential surface 25, facing the cutaway portion 26 in the side-viewing direction S resides within the depth of field of the side-viewing capturing optical system 47.

The side-viewing objective lens 28 and the side lighting lens 29 are flush with the different surfaces, the first surface 32 and the second surface 33, respectively. Accordingly, a direction of the illumination light coming out of the side lighting lens 29 crosses the side-viewing direction S.

Figure 4:
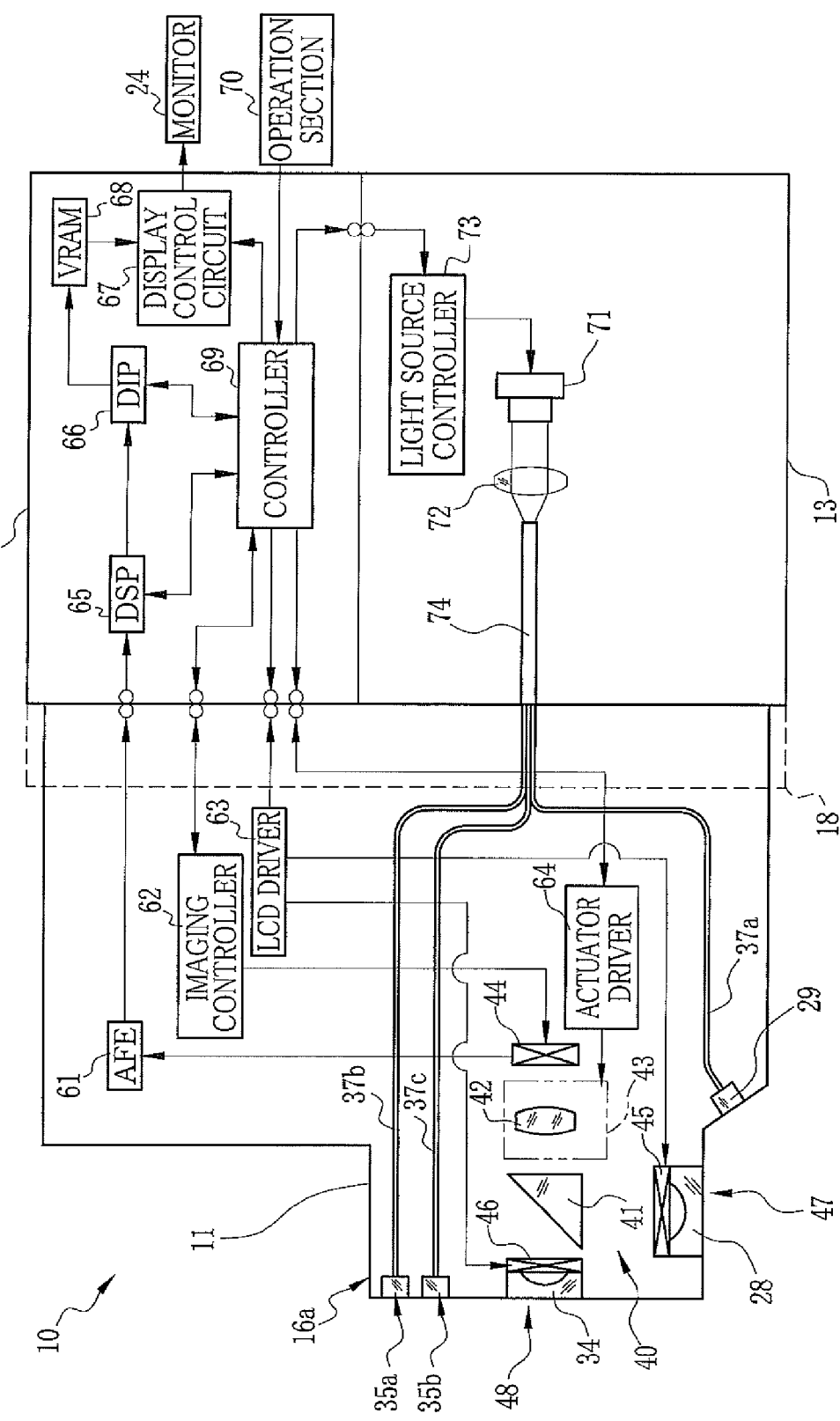
FIG. 4 is a block diagram of an electric configuration of an electronic endoscope system of the first embodiment.

In FIG. 4, the electronic endoscope 11 is provided with an AFE 61, an imaging controller 62, the LCD driver 63, and the actuator driver 64 in addition to the imaging section 40. The imaging signal from the CCD 44 is sent to the AFE 61. The AFE 61 is composed of a correlated double sampling circuit (CDS), an automatic gain control circuit (AGC), and an A/D converter (all not shown). The CDS performs correlated double sampling to the imaging signal outputted from the CCD 44 to remove noise caused by the CCD 44. Then, the AGC amplifies the imaging signal.

The imaging controller 62 is connected to a controller 69 in the processor device 12 when the electronic endoscope 11 is connected to the processor device 12. The imaging controller 62 sends a drive signal to the CCD 44 when commanded by the controller 69. In response to the drive signal, the CCD 44 outputs an imaging signal to the AFE 61 at a predetermined frame rate.

The processor device 12 is provided with a digital signal processor (DSP) 65, a digital image processor (DIP) 66, a display control circuit 67, a VRAM 68, the controller 69, an operation section 70, and the like.

The controller 69 controls the operation of the whole processor device 12. The DSP 65 performs various signal processes to the imaging signal, outputted from the AFE 61 of the electronic endoscope 11, to generate image data. The signal processes include color separation, color interpolation, gain correction, white balance adjustment, and gamma correction. The image data is inputted to a working memory of the DIP 66. The DSP 65 also generates ALC data used for automatic light control (ALC) of the illumination light quantity and inputs the ALC data to the controller 69. The ALC data includes, for example, an average brightness value that is an average of brightness of each pixel in the image data.

The DIP 66 performs various image processes to the image data generated in the DSP 65. The image processes include electronic magnification, color enhancement, and edge enhancement. After being subjected to the image processes, the image data is temporarily stored as the observation image in the VRAM 68, and then inputted to the display control circuit 67. The display control circuit 67 selects and retrieves the observation image from the VRAM 68 and displays the observation image on the monitor 24.

The operation section 70 is composed of well-known input devices, for example, an operation panel provided to a housing of the processor device 12, a mouse, and a keyboard. The controller 69 controls the operation of each section of the electronic endoscope system 10 in response to an operation signal from the operation section 70 or the handling section 17 of the electronic endoscope 11.

The light source device 13 is provided with a light source 71, a condenser lens 72, a light source controller 73, and an optical fiber 74. The light source 71 is a white light source composed of a xenon tube or the like. The white light supplied from the light source 71 is guided to the optical fiber 74 through the condenser lens 72 and the like. The optical fiber 74 is connected to each of the light guides 37a to 37c of the electronic endoscope 11 through the connector 18. The white light from the light source 71 is incident on the lighting lenses 29, 35a, and 35b through the respective light guides 37a to 37c. The white light, being the illumination light, is applied from the lighting lenses 29, 35a, and 35b to the target. The light source controller 73 controls ON/OFF timing of the light source 71 in response to a control signal or a synchronization signal inputted from the controller 69 of the processor device 12. Note that an illumination switching section may be provided. The illumination switching section transmits the illumination light to one of the side and front lighting optical systems depending on the observation mode.

In addition to the AFE 61 and the imaging controller 62, the LCD driver 63 and the actuator driver 64 are connected to the controller 69 when the electronic endoscope 11 is connected to the processor device 12. The LCD driver 63 controls each of the LCD panels 45 and 46 to switch between the passing state and the blocking state when commanded by the controller 69.

The actuator driver 64 controls the actuator 53 to move the varifocal lens 42 to the normal observation position or the magnifying observation position when commanded by the controller 69.

Figure 5A:
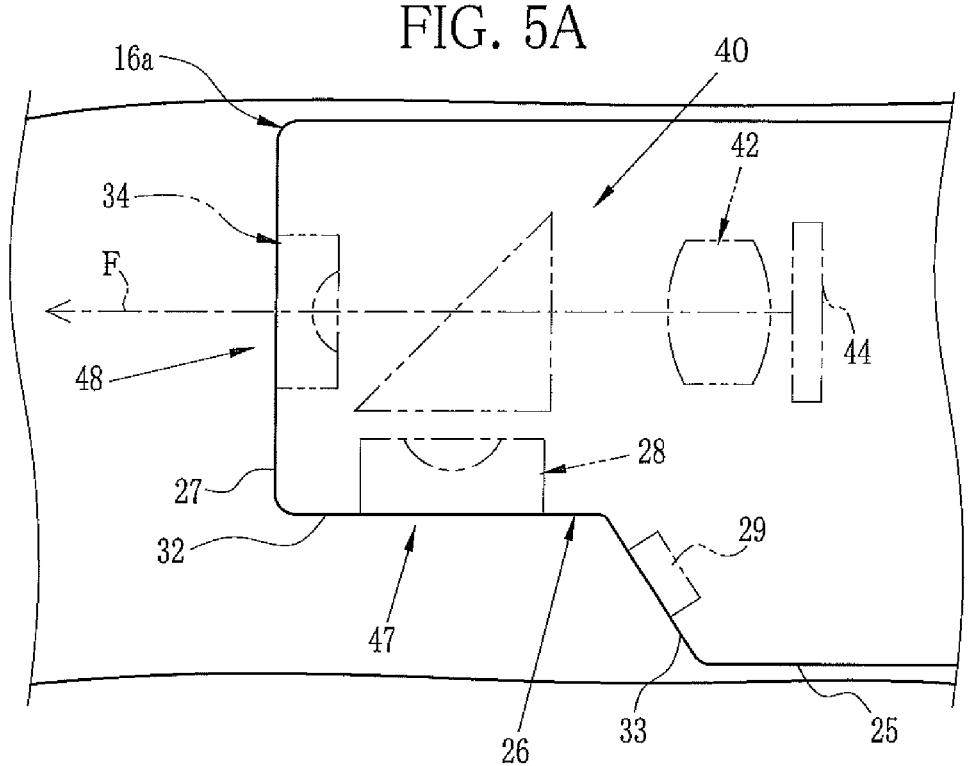
FIGS. 5A and 5B are explanatory views describing switching between a side-viewing observation mode and a front-viewing observation mode.
Figure 5B:
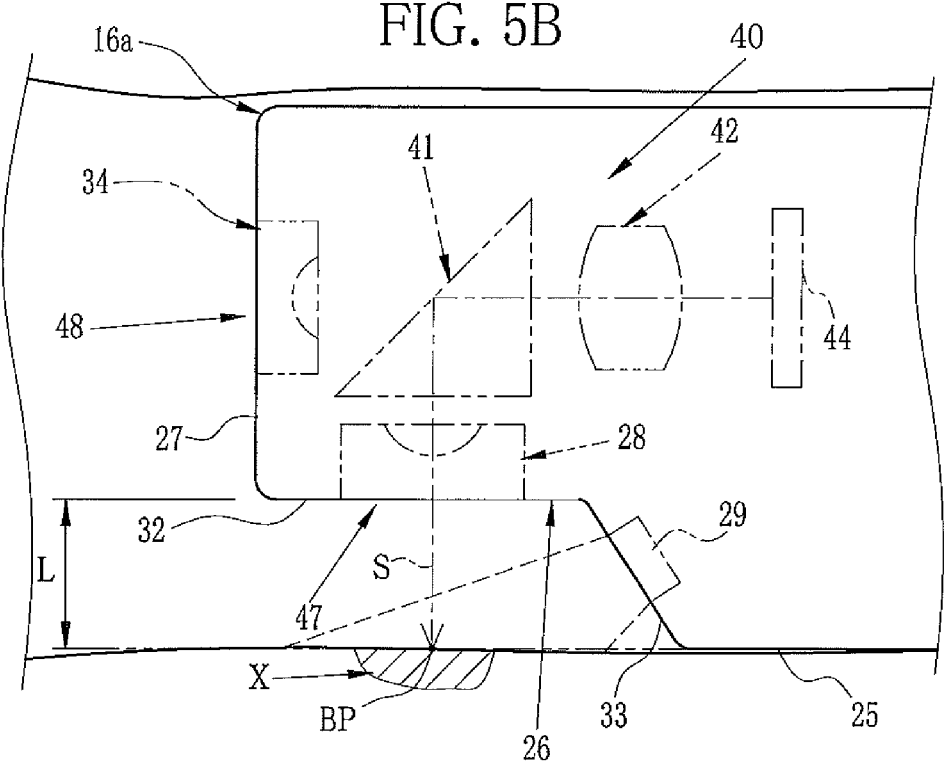

An operation of the above-described configuration is described with reference to FIGS. 5A and 5B. When the insert section 16 is inserted into the subject to observe a target with the electronic endoscope 11, in an initial setting, the front-viewing observation mode is selected. The varifocal lens 42 is at a minimum focal length, allowing the normal observation. In this state, with the use of the front-viewing capturing optical system 48, an image of the front target is formed on the CCD 44. The image is displayed as an observation image on the monitor 24.

In the normal observation in the front-viewing direction F, when an abnormal region X (see FIG. 5B), for example, a lesion is found in the subject, the operation section 70 is operated to switch from the front-viewing observation mode to the side-viewing observation mode. When the side-viewing observation mode is selected, the controller 69 controls the LCD driver 63 to put the LCD panel 45 into the passing state, and the LCD panel 46 into the blocking state. Note that by moving the varifocal lens 42, the magnifying observation can be performed in the front-viewing observation mode.

In the normal observation in the side-viewing observation mode, the extension, of the outer circumferential surface 25, facing the cutaway portion 26 in the side-viewing direction S resides within the depth of field of the side-viewing capturing optical system 47. Accordingly, the surface of the side target coinciding with the extension of the outer circumferential surface 25 is in focus. In this state, the normal observation in the side-viewing direction S is performed with the side-viewing capturing optical system 47. The abnormal region X is positioned within the field of view of the side-viewing capturing optical system 47 and observed.

When a finer observation image of the abnormal region X is needed, the operation section 70 switches from the normal observation to the magnifying observation. The controller 69 controls the actuator driver 64 to move the varifocal lens 42 from the normal observation position to the magnifying observation position. This extends the focal length, allowing the magnifying observation with the side-viewing capturing optical system 47. As shown in FIG. 5B, the best focus position BP of the side-viewing capturing optical system 47 resides on the extension, of the outer circumferential surface 25, facing the cutaway portion 26 in the side-viewing direction S, when the magnifying observation is performed. Accordingly, when a region close to the abnormal region X is in contact with the outer circumferential surface 25, the abnormal region X coincides with the extension of the outer circumferential surface 25. Thereby, the best focus position BP of the side-viewing capturing optical system 47 coincides with the surface of the abnormal region X.

As described above, the electronic endoscope 11 eliminates the need of hood, on the distal portion 16a, for ensuring a predetermined distance between the target's surface and the distal end surface 27. As a result, the diameter of the distal portion 16a is reduced. In the imaging section 40, the image of the image light of the side target taken in by the side-viewing capturing optical system 47 and the image of the image light of the front target taken in by the front-viewing capturing optical system 48 are formed on the CCD 44 through the single varifocal lens 42 shared by the side-viewing and front-viewing capturing optical systems 47 and 48. This reduces the number of parts and further reduces the size of the distal portion 16a. Because the illumination direction of the side lighting lens 29 crosses the side-viewing direction S in which the side-viewing capturing optical system 47 takes in the image light, the illumination light illuminates the side target irrespective of the distance between the side-viewing capturing optical system 47 and the side target.

Note that, in the first embodiment, the varifocal lens 42 remains in the normal observation position (the minimum focal length) when the front-viewing observation mode is switched to the side-viewing observation mode. Alternatively, the varifocal lens 42 may be moved from the normal observation position to the magnifying observation position in response to the switching of use from the LCD panel 46 to the LCD panel 45. Thus, the normal observation is automatically switched to the magnifying observation when the front-viewing observation mode is switched to the side-viewing observation mode.

In the first embodiment, the switching between the side-viewing and front-viewing observation modes is carried out by the LCD panels 45 and 46. Alternatively, each of the side-viewing capturing optical system and the front-viewing capturing optical system may incorporate a light shielding plate and a mechanism for moving the light shielding plate to shield the light in one of the side-viewing capturing optical system and the front-viewing capturing optical system. Alternatively, an iris diaphragm mechanism capable of switching between a fully open state and a closed state may be used. In the first embodiment, the prism 41 with the half mirror surface 41a is used as an optical path combiner or the optical path changer constituting the side-viewing capturing optical system 47. Instead, a plate-like half mirror may be used.

In the first embodiment, the varifocal lens 42 is positioned between the prism 41 and the CCD 44. Alternatively, the varifocal lens 42 may be positioned between the side-viewing objective lens 28 and the prism 41. The varifocal lens 42 may be disposed in any position as long as the focal length of the side-viewing capturing optical system 47 varies with the movement of the varifocal lens 42. In the first embodiment, the distal portion 16a is provided with both the side-viewing capturing optical system 47 and the front-viewing capturing optical system 48. The distal portion 16a may be provided only with the side-viewing capturing optical system 47 and omit the front-viewing capturing optical system 48. In this case, for example, the front-viewing objective lens 34, the front lighting lenses 35a and 35b, the air/water nozzle 36, and the light guides 37b and 37c are omitted in the electronic endoscope system 10 of the first embodiment. When the distal portion 16a is provided only with the side-viewing capturing optical system 47, a prism with a full-reflection mirror surface or a plate-like mirror may be used. Any member may be used as long the light in the side-viewing direction S is reflected to be incident on the CCD 44.

Figure 6:
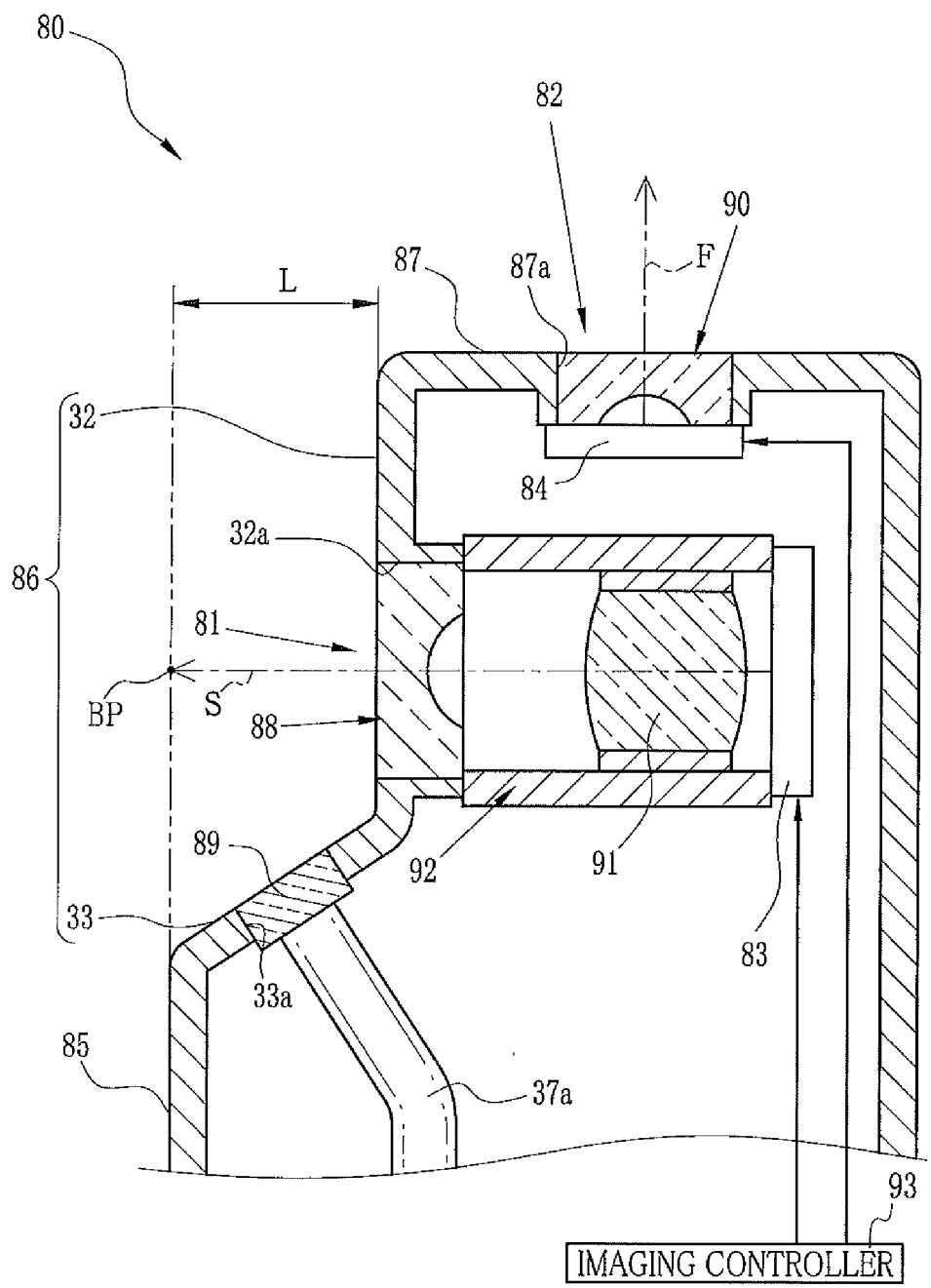
FIG. 6 is a cross-sectional view of a distal portion of another embodiment.

In the first embodiment, the side-viewing capturing optical system 47 and the front-viewing capturing optical system 48 share the single prism to form the image(s) on the single CCD 44. The imaging section 40, serving both as the side-viewing capturing optical system 47 and the front-viewing capturing optical system 48, is incorporated in the distal portion 16a. Alternatively, like a distal portion 80 of an electronic endoscope shown in FIG. 6, a side-viewing capturing optical system 81 and a front-viewing capturing optical system 82 may be provided separately. The side-viewing capturing optical system 81 and the front-viewing capturing optical system 82 are provided with CCDs 83 and 84, respectively. The CCDs 83 and 84 may form their respective images selectively or simultaneously.

In the electronic endoscope of the second embodiment, a distal portion 80a is formed with a distal end surface 87 and a narrow portion or cutaway portion 86 having a part of an outer circumferential surface (cylindrical outer surface) 85 (in other words, a part of the distal portion 80a including the outer circumferential surface 85) cut away or removed. The distal end surface 87 is a front end surface of the distal portion 80. The cutaway portion 86 is provided with a side-viewing objective lens 88 constituting the side-viewing capturing optical system 81, and a side lighting lens 89 being the side lighting optical system. An optical axis of the side-viewing objective lens 88 extends in the side-viewing direction S.

The cutaway portion 86 is composed of the first and second surfaces 32 and 33 similar to the cutaway portion 26 of the first embodiment. The side-viewing objective lens 88 is attached to the image capture window 32a formed on the first surface 32 such that an incident surface of the side-viewing objective lens 88 is flush with the first surface 32. The side-viewing objective lens 88 takes in the image light in the side-viewing direction S. The side lighting lens 89 is attached to the lighting window 33a formed on the second surface 33. The side lighting lens 89 applies the illumination light, guided by the light guide 37a, to an observation area of the side-viewing capturing optical system 81.

The distal end surface 87 is connected to the front end of the first surface 32 of the cutaway portion 86. The distal end surface 87 is planar and orthogonal to the insertion direction. The distal end surface 87 is provided with a front-viewing objective lens 90 that constitutes the front-viewing capturing optical system 82. An optical axis of the front-viewing objective lens 90 extends in the front-viewing direction F parallel with the insertion direction. The front-viewing objective lens 90 is attached to an image capture window 87a formed on the distal end surface 87 such that an incident surface of the front-viewing objective lens 90 is flush with the distal end surface 87. The front-viewing objective lens 90 takes in the image light of the front target in the front-viewing direction F. Note that the distal portion 80 is provided with a forceps outlet, a water jet outlet, an air/water nozzle, a front lighting lens, and the like (all not shown), similar to the distal portion 16a of the first embodiment.

The side-viewing capturing optical system 81 is composed of the side-viewing objective lens 88 and a varifocal lens 91. The front-viewing capturing optical system 82 has the front-viewing objective lens 90. The varifocal lens 91 and a lens moving mechanism 92 constitute the focal length changer for varying the focal length of the side-viewing capturing optical system 81. The varifocal lens 91 is moved between the normal observation position and the magnifying observation position. The lens moving mechanism 92 is composed of a lens holder, a guide member, an actuator, and the like, similar to the lens moving mechanism 43 of the first embodiment. An actuator driver (not shown) is connected to the actuator of the lens moving mechanism 92. The actuator driver controls the actuator to move the varifocal lens 91 to the normal observation position or the magnifying observation position when commanded by the controller 69 of the processor device 12.

In the distal portion 80, similar to the distal portion 16a of the first embodiment, the distance L between the side-viewing objective lens 88 and an extension (virtual extended line) of the outer circumferential surface 85 is equivalent to a depth (cut-away amount) of the cutaway portion 86 in the side-viewing direction S. The distance L is set such that the best focus position BP of the side-viewing capturing optical system 81 resides on the extension, of the outer circumferential surface 85, facing the cutaway portion 86 in the side-viewing direction S, when the varifocal lens 91 is in the magnifying observation position. On the other hand, when the varifocal lens 91 is in the normal observation position, the extension of the outer circumferential surface 85 resides within the depth of field of the side-viewing capturing optical system 47.

The CCD 83 for the side-viewing observation is disposed behind the varifocal lens 91. The CCD 84 for the front-viewing observation is disposed behind the front-viewing objective lens 90. The CCDs 83 and 84 are fixed inside the distal portion 80. The light from the side-viewing capturing optical system 81 is incident on a light receiving surface of the CCD 83. The light from the front-viewing capturing optical system 82 is incident on a light receiving surface of the CCD 84. An imaging controller 93 and an AFE (not shown) are connected to each of the CCDs 83 and 84.

In this embodiment, the imaging controller 93 functions as the switcher for switching from the side-viewing capturing optical system 81 to the front-viewing capturing optical system 82 and vice versa. Namely, the imaging controller 93 sends a drive signal to one of the CCDs 83 and 84, when commanded by the controller 69. The CCD 83 or 84 which received the drive signal outputs an imaging signal to the AFE. Thereby, the image light captured with one of the side-viewing capturing optical system 81 and the front-viewing capturing optical system 82 is formed into the observation image.

The distance L is set such that the extension, of the outer circumferential surface 85, facing the cutaway portion 86 in the side-viewing direction S resides within the depth of field of the side-viewing capturing optical system 81 in the normal observation. This enables the side-viewing capturing optical system 81 to focus on the target's surface, in a manner similar to the first embodiment. The distance L is set such that, in the magnifying observation, the best focus position BP resides on the extension, of the outer circumferential surface 85, facing the cutaway portion 86 in the side-viewing direction S. Thereby, the best focus position of the side-viewing capturing optical system 81 coincides with the target's surface, in a manner similar to the first embodiment.

In the second embodiments, the distal portion 80 is provided with both the side-viewing capturing optical system 81 and the front-viewing capturing optical system 82. The distal portion may be provided only with the side-viewing capturing optical system 81. In this case, for example, the front-viewing capturing optical system 82 and the CCD 84 for the front-viewing observation may be omitted in the configuration of the second embodiment.

In the above embodiments, the lens moving mechanism is provided with the lens holder, the guide member, and the actuator. Alternatively, the lens moving mechanism may be provided with a cam member for transforming rotary motion into linear motion to move the varifocal lens forward and backward and a drive source, for example, a stepping motor for rotating the cam member. In the above embodiments, the solenoid is used as the actuator for the lens moving mechanism. An actuator of any configuration may be used as long as the actuator moves the varifocal lens forward and backward. For example, a piezoelectric actuator using a piezoelectric element may be used.

In the above embodiments, the CCD is used as the image sensor for the side-viewing capturing optical system and the front-viewing capturing optical system. Alternatively, a CMOS may be used. In the above embodiments, for the sake of convenience in description, each of the front-viewing objective lens, the side-viewing objective lens, and the varifocal lens is illustrated as a single optical lens. In practice, it is common that each of the front-viewing objective lens, the side-viewing objective lens, and the varifocal lens is composed of lens elements to correct aberration and the like.

Various changes and modifications are possible in the present invention and may be understood to be within the present invention.

What is claimed is:

1. An electronic endoscope having an insert section to be inserted into a subject, comprising:
   a cutaway portion included in a distal portion of the insert section, the cutaway portion including a first surface formed from a distal end surface of the distal portion in parallel to a central axis of the insert section and having a part of an outer circumferential surface of the distal portion cut away, and a second surface inclined with respect to the central axis and connected to the first surface;
   a front-viewing capturing optical system, provided to be exposed from the distal end surface, for transmitting a first incident light in a front-viewing direction in parallel to the central axis;
   a front lighting optical system, provided to be exposed from the distal end surface, for applying a first illumination light to a first target observed with the front-viewing capturing optical system;
   an image sensor for capturing an image of a first transmitted light from the front-viewing capturing optical system;
   a side-viewing capturing optical system, provided to be exposed from the first surface, for transmitting a second incident light in a side-viewing direction orthogonal to the central axis;
   an optical path changer for reflecting a second transmitted light from the side-viewing capturing optical system towards the image sensor, and for transmitting the first transmitted light to the image sensor;
   a side lighting optical system, provided to be exposed from the second surface, for applying a second illumination light to a second target observed with the side-viewing capturing system;
   a forceps outlet provided to be exposed from the second surface, a medical instrument being projected and retracted from the forceps outlet;
   a focal length changer for changing a focal length of the side-viewing capturing optical system between a focal length for normal observation and a focal length for magnifying observation, wherein a focus position of the side-viewing capturing optical system in the magnifying observation resides on an extension of the outer circumferential surface, the extension facing the cutaway portion in the side-viewing direction, and the extension of the outer circumferential surface resides within a depth of field of the side-viewing capturing optical system in the normal observation; and
   a switcher for passing light from one of the front-viewing capturing optical system and the side-viewing capturing optical system and blocking light from the other of the front-viewing capturing optical system and the side-viewing capturing optical system.

2. The electronic endoscope of claim 1, wherein the side-viewing capturing optical system includes a side-viewing objective lens provided to be exposed from the second surface, for capturing a first image light in the side-viewing direction.

3. The electronic endoscope of claim 1, wherein the switcher is an LCD panel provided to each of the front-viewing capturing optical system and the side-viewing capturing optical system, and the LCD panel is switchable between a blocking state and a passing state, and the LCD panel blocks the light in the blocking state and passes the light in the passing state.

4. The electronic endoscope of claim 1, wherein the focal length changer is composed of a varifocal lens and a varifocal lens moving section for moving the varifocal lens along an optical axis direction.

5. The electronic endoscope of claim 4, wherein the varifocal lens is disposed between the optical path changer and the image sensor.

6. The electronic endoscope of claim 1, wherein the front-viewing capturing optical system includes a front-viewing objective lens, provided to be exposed from the distal end surface, for capturing a second image light in the front-viewing direction.

7. The electronic endoscope of claim 1, wherein the optical path changer is a half mirror.

8. The electronic endoscope of claim 1, wherein an optical axis of the side-viewing capturing optical system, an optical axis of the front-viewing capturing optical system and an optical axis of the side lighting optical system resided in a cross section including the central axis.

9. The electronic endoscope of claim 1, further comprising:
   a water jet outlet disposed in the second surface, wherein the side lighting optical system is put between the forceps outlet and the water jet outlet in the second surface.

10. The electronic endoscope of claim 1, wherein a pair of the front lighting optical system is disposed so as to put the front-viewing capturing optical system there between in the distal end surface.

11. The electronic endoscope of claim 1, further comprising:
    an air/water nozzle, disposed between the front-viewing capturing optical system and one of the pair of the front lighting optical system in the distal end surface, an nearer to the first surface in the distal end surface, for spraying air or water to the front-viewing capturing optical system.

* * * * *